(12) United States Patent
Hermansson et al.

(10) Patent No.: US 7,347,846 B2
(45) Date of Patent: Mar. 25, 2008

(54) ELASTIC ABSORBENT PANTS HAVING AN ELASTIC MATERIAL SECURED IN AN UNSTRETCHED STATE TO AN ABSORBANT CORE OR CORE PACK

(75) Inventors: Kent Hermansson, Västra Frölunda (SE); Niclas Norrby, Göteborg (SE); Catarina Linnér, Lindome (SE)

(73) Assignee: SCA Hygiene Products AB, Gothenburg (SE)

( * ) Notice: Subject to any disclaimer, the term of this patent is extended or adjusted under 35 U.S.C. 154(b) by 279 days.

(21) Appl. No.: 10/367,878

(22) Filed: Feb. 19, 2003

(65) Prior Publication Data
US 2003/0220622 A1    Nov. 27, 2003

Related U.S. Application Data

(60) Provisional application No. 60/357,105, filed on Feb. 19, 2002.

(51) Int. Cl.
*A61F 13/20* (2006.01)
(52) U.S. Cl. ............... 604/385.3; 604/385.29; 604/385.22; 604/385.23; 604/385.28; 604/373; 604/357; 604/385.01; 604/358; 156/183; 156/344; 428/198
(58) Field of Classification Search ............ 604/385.3, 604/385.22–385.29, 373, 367, 385.01, 358, 604/357; 156/183, 344; 428/198
See application file for complete search history.

(56) References Cited

U.S. PATENT DOCUMENTS

| | | | |
|---|---|---|---|
| 4,050,462 A | * | 9/1977 | Woon et al. ............ 604/365 |
| 4,895,568 A | * | 1/1990 | Enloe ............... 604/385.27 |
| 4,938,757 A | * | 7/1990 | Van Gompel et al. ...... 604/396 |
| 5,236,430 A | * | 8/1993 | Bridges .................. 604/396 |
| 5,440,764 A | | 8/1995 | Matsushita |
| 5,899,896 A | * | 5/1999 | Suprise et al. ............. 604/391 |
| 6,083,212 A | * | 7/2000 | Kumasaka ............ 604/385.29 |
| 6,149,637 A | | 11/2000 | Allen et al. |

FOREIGN PATENT DOCUMENTS

| WO | WO 9519258 A1 | * | 7/1995 |
|---|---|---|---|
| WO | 00/19951 | | 4/2000 |

* cited by examiner

*Primary Examiner*—Tatyana Zalukaeva
*Assistant Examiner*—Ginger Chapman
(74) *Attorney, Agent, or Firm*—Buchanan Ingersoll & Rooney PC

(57) ABSTRACT

Absorbent pants with a longitudinal direction and a transverse direction at right angles to the longitudinal direction and having an absorption core arranged between a liquid-tight cover sheet and a liquid-permeable cover sheet. The diaper pants have a front portion, a rear portion and an intermediate crotch portion, and a front edge and a rear edge extending substantially in the transverse direction and forming a waist opening, two side edges extending substantially in the longitudinal direction and forming two leg openings. An elastic sheet material is arranged at least along the waist opening of the diaper pants and extends at least from the waist opening to the leg openings, the elastic sheet material being secured to the absorption core in a substantially unstretched state.

63 Claims, 2 Drawing Sheets

ELASTIC ABSORBENT PANTS HAVING AN ELASTIC MATERIAL SECURED IN AN UNSTRETCHED STATE TO AN ABSORBANT CORE OR CORE PACK

CROSS-REFERENCE TO RELATED APPLICATIONS

The present application claims the benefit of U.S. Provisional Application No. 60/357,105, filed in the United States on Feb. 19, 2002, the entire contents of which are hereby incorporated herein by reference.

TECHNICAL FIELD

The invention relates to diaper pants, with a longitudinal direction and a transverse direction at right angles to the longitudinal direction and comprising an absorption core arranged between a liquid-tight cover sheet and a liquid-permeable cover sheet, the absorbent pants having a front portion, a rear portion and an intermediate crotch portion, a front edge and a rear edge extending substantially in the transverse direction and forming a waist opening having an unextended circumference and an extended circumference, two side edges extending substantially in the longitudinal direction and forming two leg openings.

BACKGROUND

The main components in diaper pants are usually an absorption core which is arranged between two cover sheets, one of which is a liquid barrier sheet, for example a plastic film, and the other a liquid-permeable cover sheet, for example a nonwoven sheet. Further components, such as inner barriers, for example raised edge barriers, arranged in connection with the liquid-permeable cover sheet, or textile-like outer covers arranged outside the liquid barrier sheet can also be present. The absorbent pants are designed with a front portion which, during use, is directed forwards on the user and lies across the latter's groin area, a rear portion which, during use, is directed rearwards on the user and lies across the latter's buttocks, and a crotch portion which is arranged between the front portion and the rear portion and is intended to be positioned at the user's crotch. The front portion, the rear portion and the crotch portion together form absorbent pants or briefs with two leg openings and a waist opening. The absorption core is usually arranged substantially centrally between the leg openings and extends at least over the crotch portion. The portions of the absorbent pants which, during use, are arranged across the user's hips are generally free from absorption material. These portions consist, for example, of parts of one or both of the cover sheets, of a separate outer cover, or of separate material pieces usually called side panels.

In order to ensure that the absorbent pants will fit a user's body shape and body size like an article of clothing, and in order to form closure seals preventing leakage around the leg openings and the waist openings, the absorbent pants are generally also provided with elastic members in the form of elastic threads or bands. The elastic threads and bands are generally secured, in a continuous process and in the stretched state, to one or more components of the absorbent pants, generally to at least one cover sheet. By means of securing stretched elastic members, for example to a cover sheet, it is possible also to give a nonelastic material sheet elastic properties. The elastic members are kept stretched during production of the known diaper pants. When the individual diaper pants are cut out from a continuous production web, the stretching of the elastic members ceases and they are able to gather together into their unstretched state. In doing so, the components secured to the elastic members are also gathered together. This means that the finished absorbent pants have a creased appearance, at least in the areas around the elastic members. In addition, the elastic members give the absorbent pants a three-dimensional form which makes them difficult to fold and package.

In order to achieve a good fit of the known diaper pants and to allow the diaper pants to be used by persons with different body shapes and body sizes, the diaper pants are often provided with a large number of elastic members which run parallel across the front and rear portions of the absorbent pants. Although such an arrangement functions fairly well from the technical point of view, the many elastic members give the known diaper pants a particularly creased and baggy appearance. This is a negative factor for various reasons. The greatest disadvantage is that it is difficult to conceal diaper pants of this kind under normal clothes, which can be very embarrassing, especially for adult users of diaper pants. The creased appearance also strengthens the immediate impression that the absorbent article is in fact a diaper, which is perceived as a negative factor by adult incontinence sufferers. It is therefore desirable to produce diaper pants which are perceived and appear more as underpants than as a diaper. Another disadvantage of using the creased diaper pants is that folds and creases can cause discomfort in the form of chafing and irritation of the user's skin.

A way of achieving an improved fit and of avoiding the use of a large number of stretched elastic members is to make the side panels of diaper pants from elastic material, for example elastic nonwoven, or elastic laminate. However, the main problem of the diaper pants with elastic side panels which have hitherto been proposed is that they are complicated to produce because they necessitate the handling of separate elastic material pieces at high production speeds. Moreover, with elastic side panels, it is possible only to obtain limited size fit and shape fit of the diaper pants because large parts of the front portion and rear portion of the absorbent pants remain nonelastic.

There is therefore a great need for absorbent diaper pants which are comfortable to wear, sit securely in place and can be concealed under normal clothes.

SUMMARY

Elastic diaper pants have been obtained which substantially eliminate the disadvantages of previously known diaper pants of this kind. Diaper pants or absorbent pants according to embodiments of the invention are mainly distinguished by elastic sheet material which is arranged at least along the waist opening of the absorbent pants and extends the whole way from the waist opening to the leg openings, the elastic sheet material being secured to the absorption core in a substantially unstretched state.

Diaper pants according to embodiments of the invention can thus be made of material which has been joined together while in a substantially unstretched, tension-free state, i.e. with only a slight degree of elastic tensioning. An elastic material in a substantially unstretched state is herein understood as meaning that the material is stretched not more than about 5% from its completely unstretched state. This means that the finished diaper pants are smooth and have a substantially plane shape. Diaper pants thus formed can have an aesthetically pleasing appearance, are comfortable and discreet to wear, and are considerably easier to fold and package than previously known diaper pants with creased and three-dimensionally curved portions.

The elastic parts of the absorbent pants or diaper pants according to embodiments of the invention are activated when the absorbent pants are put on. The elastic portions are stretched out so that the absorbent pants can fit onto a user's body. The size of the absorbent pants can be such that the elastic portions are kept stretched during use and thus seek to draw together to their unstressed state, by which means the absorbent pants are maintained on the user's body. According to a preferred embodiment, the elastic sheet material is elastically extensible in more than one direction, which is advantageous with respect to the fit of the absorbent pants.

It has been found that, for absorbent pants to be able to be put on and taken off easily and comfortably, the extensibility should be sufficient to allow the pants to be stretched out across the user's hips. The extensibility should be such that the pants can be stretched past the hips and such that they can be pulled up over the hips simply by gripping the pants at the waist edge. In absorbent pants which can be put on easily and comfortably, the extensibility of the elastic sheet material should be at least 80% in the transverse direction of the absorbent pants and preferably at least 100% in the transverse direction of the absorbent pants.

As regards the fit of the absorbent pants, it is also advantageous if the extensibility of the elastic sheet material in the longitudinal direction of the absorbent pants, i.e., in a direction parallel to a line between the rear edge and the front edge of the absorbent pants, is at least 80% and preferably at least 100%.

Elastic extensibility here refers to the lengthening in the direction of extension which the material permits without plastically deforming or bursting. If a material is to be considered as being elastically extensible, it is also necessary for the material, when extension ceases, to gather together and seek to recover its original extent in the direction of extension. A fully elastic material returns completely to the unextended state, while a less elastic material remains slightly stretched even when the stretching force ceases. For the purposes of the invention, it is expedient that the elastic material web can return to an extent which is at most 150% of the unstretched material web and preferably at most 120% thereof.

The elastic sheet material can advantageously be arranged in the form of outer pants which support the absorption core. Such an embodiment affords diaper pants which have an extremely good fit.

In order to further improve the fit and the leaktightness of the diaper pants, elastic members can be arranged around the waist opening and thus form waist elastic.

Correspondingly, elastic members can be arranged around the leg openings and form leg elastic which, during use of the absorbent pants, fits round the user's legs. In addition to contributing to an improved fit and increased leaktightness, leg elastic and waist elastic give the absorbent pants an appearance more like briefs.

The elastic members in the waist elastic and leg elastic are preferably arranged on the absorbent pants in a substantially unstressed state and expediently with a degree of extensibility of at most about 10% and preferably at most about 5%.

On application of elastic members with low prestressing, or no prestressing, it is preferred that the elastic members be secured in such a way that the elasticity in the elastic members is not inhibited. This can be done, for example, by using an elastic adhesive, by gluing in a stretchable pattern along the elastic members, or by intermittent welding. Examples of stretchable adhesive patterns are spot gluing, spray gluing, and adhesive applied in the form of adhesive strands arranged across the elastic members.

In order to ensure that the absorbent pants are maintained in the correct position on the user's body and do not slip down across the user's hips even when they have absorbed a large amount of bodily excretions, the absorbent pants should be able to support a weight of at least 200 g (approximately 2 N) when the absorbent pants are intended for persons with mild incontinence. Persons suffering from what is generally called mild incontinence are only urine-incontinent and are generally able to change their incontinence protection as soon as the opportunity arises after urination. By contrast, persons with severe incontinence are often not able to determine when the bladder has emptied and are therefore often not in a position to change their incontinence protector. In addition, severe incontinence quite often involves a combination of urinary incontinence and fecal incontinence, which means that considerably greater amounts of bodily excretions generally have to be retained in an incontinence protector for severely incontinent persons. Such an incontinence protector should therefore be able to support a weight of 1000 g (approximately 10 N).

According to one embodiment of the invention, the absorbent pants include a core pack comprising a liquid barrier sheet, an absorption core and a liquid-permeable inner sheet, said core pack being secured with the liquid barrier sheet towards the elastic sheet material.

According to another embodiment of the invention, the absorption core is arranged between an elastic liquid-permeable inner sheet and an elastic barrier sheet.

According to another embodiment, the absorbent pants have a longitudinal direction and a transverse direction at a right angle to the longitudinal direction, a front portion, a rear portion and an intermediate crotch portion, a front edge and a rear edge extending substantially in the transverse direction and forming a waist opening having an unextended circumference and an extended circumference, and two side edges extending substantially in the longitudinal direction and forming two leg openings. A sheet of elastic material is arranged at least along the waist opening extends at least from the waist opening to the leg openings. The sheet of elastic material being secured to the absorption core, which has absorbent material, in a substantially unstretched state.

According to another embodiment, a sheet of elastic material is arranged at least along the waist opening extending at least from the waist opening to the leg openings. A core pack includes an absorption core having absorbent material, a liquid barrier sheet, and a liquid-permeable inner sheet, with the absorption core being arranged between the liquid barrier sheet and the liquid-permeable inner sheet. The sheet of elastic material is secured to the core pack in a substantially unstretched state.

According to another embodiment, a sheet of elastic material is arranged at least along the waist opening and extending at least from the waist opening to the leg openings. A core pack includes a liquid barrier sheet, a liquid-permeable sheet, and absorption core having absorbent material, with the absorption core arranged between the liquid barrier sheet and the liquid-permeable sheet. The sheet of elastic material is secured to the core pack in a substantially unstretched state. Elastic members are secured to the sheet of elastic material with the sheet of elastic material in a substantially unstretched state and with the elastic members being extended less than about 10%.

In another embodiment, the sheet of elastic material is arranged at least along the waist opening and extending at least from the waist opening to the leg openings. The core pack includes a liquid barrier sheet, a liquid-permeable sheet, and an absorption core having absorbent material, the absorption core arranged between the liquid barrier sheet and the liquid-permeable sheet. The sheet of elastic material is secured to the core pack in a substantially unstretched state on a side of the core pack intended to face away from a wearer's body during use. A liquid-permeable inner sheet arranged at a side of the core pack intended to face the wearer in use. Elastic members are secured to the sheet of elastic material with the sheet of elastic material in a substantially unstretched state and the elastic members being extended less than about 10%.

BRIEF DESCRIPTION OF THE FIGURES

The invention will be described in greater detail below with reference to the figures in the attached drawings, in which.

DETAILED DESCRIPTION OF EMBODIMENTS

Figure 1:
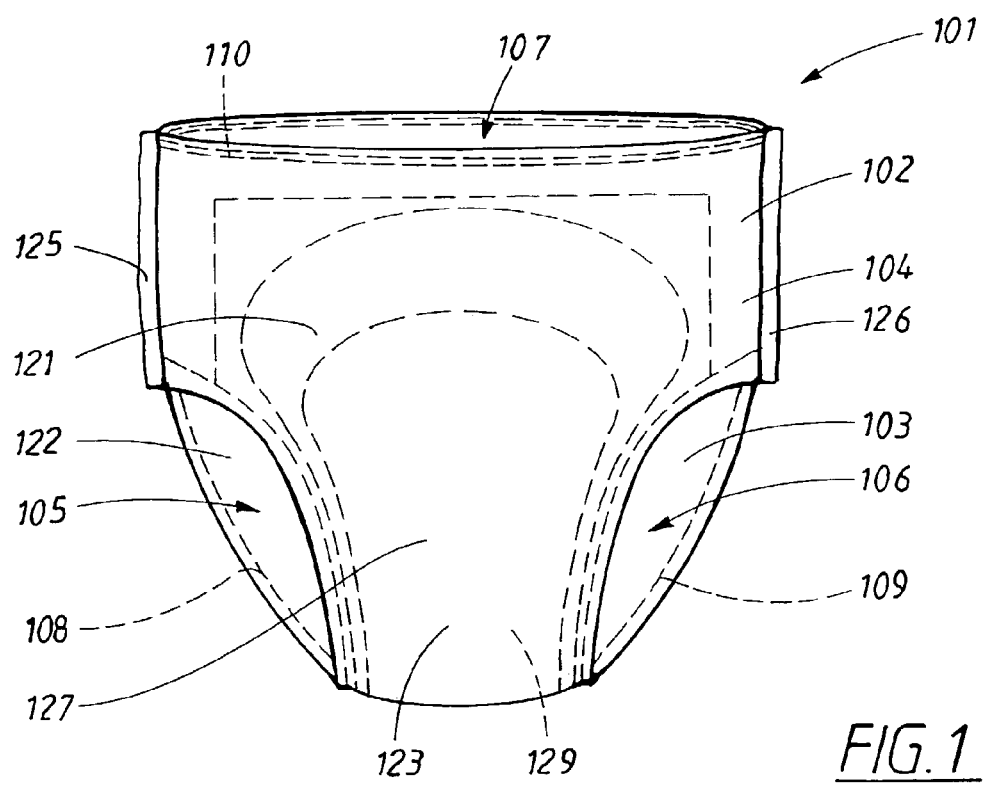
FIG. 1 shows diaper pants according to a first embodiment of the invention and comprising a core pack.

The absorbent diaper pants 101 shown in FIG. 1 comprise elastically extensible outer pants 102 which are formed by an inner elastic material sheet 103 and an outer elastic material sheet 104 which are connected to each other, for example by adhesive bonding or by welding with heat or ultrasound. Suitable elastic material sheets are different types of elastic nonwoven material. As has previously been mentioned, an elastic nonwoven suitable for use in absorbent pants according to an embodiment of the invention should be able to be stretched elastically at least 80% and preferably at least 100% in the transverse direction of the pants so that the waist opening (see below) of the pants can be widened sufficiently for the pants to be able to be pulled up across the user's hips in a convenient way. It is also advantageous if the elastic nonwoven material can also be stretched elastically in the longitudinal direction of the absorbent pants, i.e. in a direction at right angles to the transverse direction.

The material sheets included in the outer pants 102 can also be laminates. In addition, it is of course possible to use more than two sheets to form the outer pants.

The outer pants 102 have two leg openings 105, 106, and a waist opening 107 which extends in the transverse direction of the diaper pants and is formed by a front waist edge which, when the diaper pants are in use, is arranged over the user's stomach, and a rear waist edge which, during use, is arranged across the user's back.

Elastic members are arranged as leg elastic 108, 109 around the leg openings 105, 106 and as waist elastic 110 around the waist opening 107. In the illustrative embodiment shown, the elastic members 108, 109, 110 are secured between the two elastic material sheets 103, 104. However, it is possible, within the scope of the invention, to form the outer pants from just one material sheet and in this case to secure any elastic members around leg openings and waist opening only to this material sheet.

The outer pants 102 are designed with a front portion 121 which, during use, is directed forwards on the user and lies across the user's stomach, a rear portion 122 which, during use, is directed rearwards on the user and lies across the user's buttocks, and a narrower intermediate crotch portion 123 which, during use, is arranged between the user's legs. The outer pants 102 can also have two side edges or seams 125, 126 which connect the front portion 121 to the rear portion 122 between the waist opening 107 and the leg openings 105, 106 and which, during use of the diaper pants 101, are intended to be arranged across the user's hips.

A core pack 127 is secured inside the elastically extensible outer pants 102. The core pack 127 can be secured to the outer pants 102 across the whole of the common surface, or only over parts thereof. For example, the core pack 127 can be secured only along a line or a band-shaped area extending centrally across the diaper pants 101 from the front portion 121 to the rear portion 122. Alternatively, the core pack can be secured along one or more transverse lines or band-shaped areas. For example, it may be expedient to secure the core pack within a transverse attachment area in the crotch portion 123 of the diaper pants. It is also possible to secure the core pack 127 via a number of attachment points or attachment areas. The core pack 127 should be sufficiently well secured inside the outer pants 102 to ensure that it does not come loose or move out of position during use. However, it is advantageous if the core pack 127 has a certain mobility in relation to the outer pants 102, since this means that the elastic extensibility of the outer pants 102 can be better used if the extension is limited as little as possible by the core pack 127.

Figure 2:
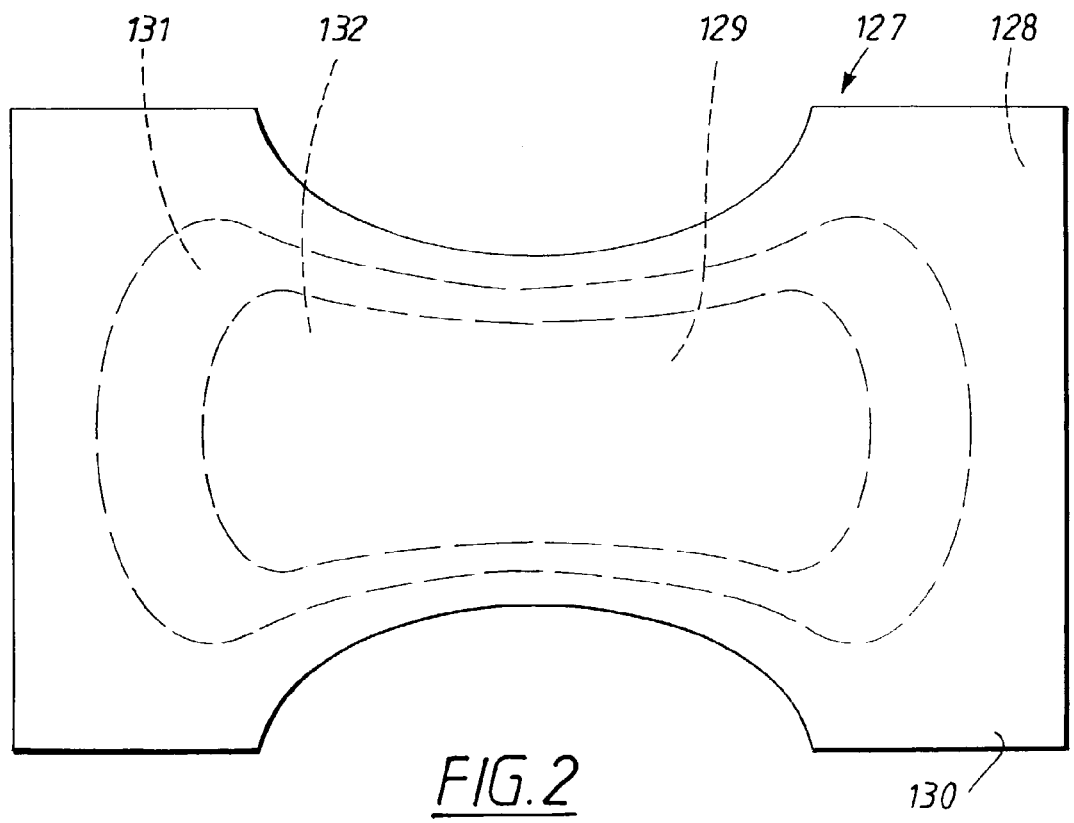
FIG. 2 shows the core pack in FIG. 1.

The core pack 127 illustrated in FIG. 2 comprises a liquid barrier sheet 128, an absorption core 129, and a liquid-permeable inner sheet 130. The core pack 127 is secured with the liquid barrier sheet 128 towards the inner elastic material sheet 103. FIGS. 1 and 2 show an absorption core 129 having two absorption sheets 131, 132 laid one upon the other, the lower absorption sheet 131 located nearest to the liquid barrier sheet 128 being slightly larger than the upper absorption sheet 132 located nearest to the inner sheet 130. In the example shown, the core pack 127 has an angular hourglass shape in the plane, the plane form of the core pack being defined by the shape of the liquid barrier sheet 128 and the liquid-permeable inner sheet 130, which together enclose the absorption core 129. It is of course possible to use the core pack 127 with another plane shape, for example the liquid barrier sheet 128 and the inner sheet 130 can have a more rounded hourglass shape, a rectangular shape, a trapezoidal shape, an oval shape, etc. Nor does the core pack need to be the size shown in the figure. For example, in the case of absorbent pants intended as protection for mild incontinence or as sanitary towels, it may be sufficient to have an absorption core 129 which is positioned mainly in the crotch portion 123 of the absorbent pants.

The liquid-permeable inner sheet 130 can be any material known for the purpose, such as a layer of nonwoven material, a perforated plastic film, net material, tow, or the like. The inner sheet 130 can of course also be a laminate of two or more sheets of the same or different material.

The liquid barrier sheet 128 can include a liquid-tight plastic film, a hydrophobic nonwoven sheet, or a nonwoven sheet which has been treated to give it liquid barrier properties, or some other flexible material sheet which has the ability to withstand liquid penetration. However, it can be advantageous if the liquid barrier sheet 128 has a certain breathability, i.e. permits the passage of water vapour through the sheet 128.

The absorption core 129 can be made up of absorbent material, such as cellulose fluff pulp, tissue, absorbent foam, etc. It is also possible for the absorption core to contain superabsorbents, i.e. polymer materials which are able to absorb body fluid corresponding to many times their own weight and form a hydrogel. Such superabsorbents are usually present in the form of particles, but fibres, flakes, granules and films are also available. Moreover, the absorption core 129 can include nonabsorbent components such as stiffening elements, shaping elements, binders, etc. Various types of liquid-receiving and liquid-distributing structures such as fibre wads, open-cell foam, spreading sheets or the like can also be included in the core pack 127.

The various components included in the core pack 127 can be connected to one another in a conventional manner, for example by adhesive bonding, or by welding with heat or ultrasound. The core pack 127 can of course contain further components in addition to those described here, for example the core pack can include a liquid transport sheets, elastic members, shape-stabilizing members, shaping elements or the like. Although the absorption core has been shown with two absorption sheets 131, 132, alternative configurations can be used. For example, a single absorption sheet may be sufficient for certain applications, while other applications may require more than two absorption sheets. The configuration of the absorption core can thus be adapted to the amount of liquid which the absorption core is expected to absorb. Likewise, as regards the size and nature of the absorption core, it can depend on which type of bodily excretions are to be absorbed and in which way the bodily excretions are discharged to the absorption core.

Figure 3:
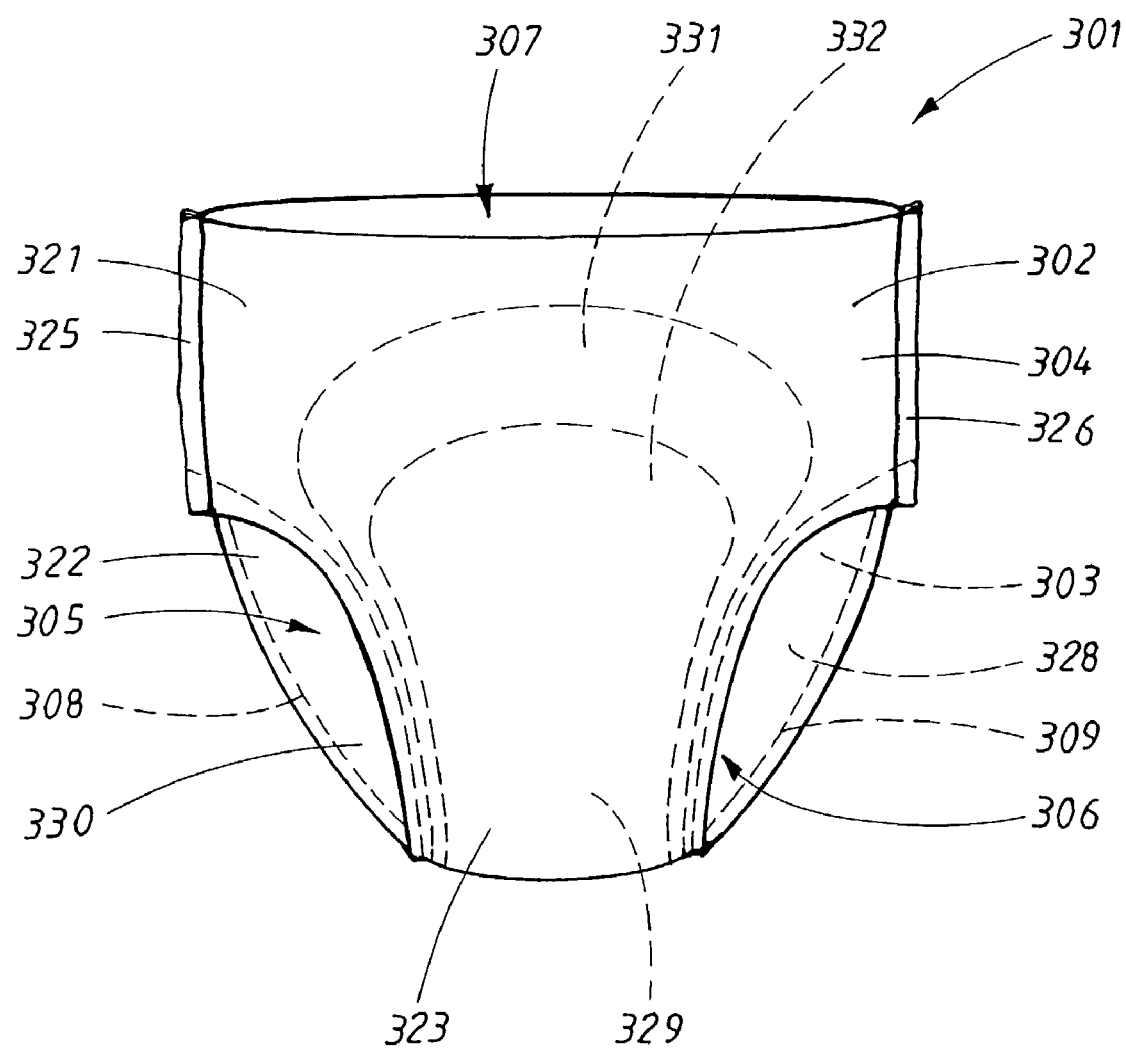
FIG. 3 shows diaper pants according to a second embodiment of the invention.

FIG. 3 shows absorbent pants or diaper pants 301 which, like the diaper pants in FIG. 1, comprise elastically extensible outer pants 302 which are formed by an inner elastic material sheet 303 and an outer elastic material sheet 304. The outer elastic material sheet 304 in this case constitutes a textile outer sheet of the diaper pants 301, and the inner elastic material sheet constitutes the liquid barrier sheet 328 in the diaper pants 301 and prevents liquid from leaking out from the diaper pants 301 during use. The outer pants 302 also include elastic members 308, 309 which are arranged around the leg openings 305, 306 of the diaper pants and which are secured between the textile outer sheet 304 of the outer pants 302 and the liquid barrier sheet 328. The textile outer sheet 304 expediently is formed of elastic nonwoven material.

The liquid barrier sheet 328 can be an elastic liquid-tight plastic film, an elastic liquid-tight nonwoven material, or the like.

In the same way as the diaper pants 101 shown in FIG. 1, the outer pants 302 are designed with a front portion 321, a rear portion 322 and a narrower crotch portion 323 lying between these. The outer pants 302 also can have two side seams 325, 326 which connect the front portion 321 to the rear portion 322 between the waist opening 307 and the leg openings 305, 306 and which, during use of the diaper pants 301, are intended to be arranged across the user's hips.

An absorption core 329 is secured inside the elastically extensible outer pants 302. The absorption core 329 can be secured to the liquid barrier sheet 328 of the outer pants 302, for example, by adhesive bonding. The absorption core 329 comprises a first liquid collection sheet 331 arranged nearest to the liquid barrier sheet 328, and a second liquid-receiving sheet 332 arranged between the liquid collection sheet 331 and a liquid-permeable inner sheet. The liquid-permeable inner sheet 330 can be a liquid-permeable nonwoven material, a perforated plastic film, a net material, or the like. The liquid-permeable inner sheet 330 can be elastic or nonelastic. In the illustrative embodiment shown, the inner sheet 330 extends across the whole of the inner side of the diaper pants and thus forms a textile inner sheet against the user's skin. In such an embodiment, the inner sheet is elastic. When using a nonelastic inner sheet, the latter can be applied only over a smaller surface of the outer pants 302, so that the absorption core 329 is covered, with minimal adverse effect on the elasticity of the outer pants 302.

Although the absorption core 329 has been shown as a two-sheet structure, it is of course possible, in the same way as in the diaper pants shown in FIG. 1, to use other types of absorption bodies.

Absorption bodies in absorbent articles for taking up body fluids usually include fibre sheets, for example of cellulose fluff pulp. It is also possible to use fibre sheets which have been bonded together with a binder, for example thermofibres. It is also possible to use polymeric gel-forming absorption materials, called superabsorbents, which can be mixed with fibres or arranged on separate carrier sheets. The design of the absorption body 409, like the choice of material, is of course dictated by the intended application and by the amount of liquid which the absorption body is expected to be able to absorb.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. Absorbent pants with a longitudinal direction and a transverse direction at a right angle to the longitudinal direction, comprising:
   a front portion, a rear portion and an intermediate crotch portion;
   a front edge and a rear edge extending substantially in the transverse direction and forming a waist opening having an unextended circumference and an extended circumference;
   two side edges extending substantially in the longitudinal direction and forming two leg openings;
   a sheet of elastic material arranged at least along the waist opening and extending at least from the waist opening to the leg openings; and
   an absorption core comprising absorbent material,
   the sheet of elastic material being secured directly to the absorption core in a substantially unstretched state.

2. The absorbent pants according to claim 1, wherein the extensibility of the sheet of elastic material is at least 80% in the transverse direction of the diaper pants.

3. The absorbent pants according to claim 1, wherein the extended circumference of the waist opening is at least 80% greater than the unextended circumference.

4. The absorbent pants according to claim 3, wherein the extensibility of the sheet of elastic material is at least 80% in the transverse direction of the diaper pants.

5. The absorbent pants according to claim 2, wherein the sheet of elastic material is also extensible in the longitudinal direction.

6. The absorbent pants according to claim 1, wherein the extensibility of the sheet of elastic material is at least 100% in the transverse direction of the diaper pants.

7. The absorbent pants according to claim 1, wherein the extended circumference of the waist opening is at least 100% greater than the unextended circumference.

8. The absorbent pants according to claim 7, wherein the extensibility of the sheet of elastic material is at least 100% in the transverse direction of the diaper pants.

9. The absorbent pants according to claim 1, wherein the sheet of elastic material forms outer pants of the absorbent article intended to face away from a wearer when the pants are worn.

10. The absorbent pants according to claim 9, wherein the outer pants comprise a liquid-impermeable material sheet.

11. The absorbent pants according to claim 9, wherein the outer pants comprise an inner elastic material sheet and an outer elastic material sheet.

12. The absorbent pants according to claim 11, wherein the inner elastic material sheet is liquid-impermeable.

13. The absorbent article as set forth in claim 11, wherein the outer elastic material sheet comprises a nonwoven elastic material or an elastic textile.

14. The absorbent pants according to claim 11, wherein elastic members are arranged between the inner elastic material sheet and the outer elastic material sheet.

15. The absorbent pants according to claim 14, wherein the elastic members are secured between the inner elastic material sheet and the outer elastic material sheet with the elastic members being extended at most about 10% and with the inner elastic material sheet and the outer elastic material sheet being substantially unstretched.

16. The absorbent pants according to claim 9, further comprising elastic members secured to the sheet of elastic material forming the outer pants with the elastic members being extended no more than about 10%.

17. The absorbent pants according to claim 9, comprising:
a liquid-permeable inner sheet arranged at a side of the absorbent core intended to face toward a wearer's body when the pants are worn.

18. The absorbent pants according to claim 17, wherein the liquid-permeable inner sheet is non-elastic.

19. The absorbent pants according to claim 17, wherein the liquid-permeable inner sheet is elastic.

20. The absorbent pants according to claim 19, wherein the elastic liquid-permeable inner sheet forms an inner surface of the absorbent pants.

21. The absorbent pants according to claim 1, wherein elastic members are arranged around the waist opening and form waist elastic and/or are arranged around the leg openings and form leg elastic.

22. The absorbent pants according to claim 20, wherein the elastic members are arranged on the absorbent pants with the elastic members being extended no more than about 10%.

23. The absorbent pants according to claim 22, wherein the extensibility of the sheet of elastic material is at least 80% in the transverse direction of the diaper pants.

24. The absorbent pants according to claim 22, wherein the extended circumference of the waist opening is at least 80% greater than the unextended circumference.

25. The absorbent pants according to claim 24, wherein the extensibility of the sheet of elastic material is at least 80% in the transverse direction of the diaper pants.

26. The absorbent pants according to claim 1, wherein the absorbent pants can support a weight of 200 grams.

27. The absorbent pants according to claim 1, wherein the absorbent pants can support a weight of 1000 grams.

28. The absorbent pants according to claim 1, wherein the sheet of elastic material is substantially unstretched and the absorbent pants have a planar shape when the pants are not being worn, and wherein the web of elastic material stretches in at least the transverse direction to fit a wearer's body when the pants are worn.

29. Absorbent pants with a longitudinal direction and a transverse direction at a right angle to the longitudinal direction, comprising:
a front portion, a rear portion and an intermediate crotch portion;
a front edge and a rear edge extending substantially in the transverse direction and forming a waist opening having an unextended circumference and an extended circumference;
two side edges extending substantially in the longitudinal direction and forming two leg openings;
a sheet of elastic material arranged at least along the waist opening and extending at least from the waist opening to the leg openings; and
a core pack including
an absorption core having absorbent material,
a liquid barrier sheet, and
a liquid-permeable inner sheet, with the absorption core being arranged between the liquid barrier sheet and the liquid-permeable inner sheet,
the sheet of elastic material being secured directly to the core pack in a substantially unstretched state.

30. The absorbent pants according to claim 29, wherein the extensibility of the sheet of elastic material is at least 80% in the transverse direction of the diaper pants.

31. The absorbent pants according to claim 29, wherein the extended circumference of the waist opening is at least 80% greater than the unextended circumference.

32. The absorbent pants according to claim 31, wherein the extensibility of the sheet of elastic material is at least 80% in the transverse direction of the diaper pants.

33. The absorbent pants according to claim 30, wherein the sheet of elastic material is also extensible in the longitudinal direction.

34. The absorbent pants according to Claim 29, wherein the extensibility of the sheet of elastic material is at least 100% in the transverse direction of the diaper pants.

35. The absorbent pants according to claim 29, wherein the extended circumference of the waist opening is at least 100% greater than the unextended circumference.

36. The absorbent pants according to claim 35, wherein the extensibility of the sheet of elastic material is at least 100% in the transverse direction of me diaper pants.

37. The absorbent pants according to claim 29, wherein the sheet of elastic medal forms outer pants of the absorbent article intended to face away from a wearer when the pants are worn.

38. The absorbent pants according to claim 37, wherein the outer pants comprise an inner elastic material sheet and an outer elastic material sheet.

39. The absorbent pants according to claim 38, wherein the inner elastic material sheet is liquid-impermeable.

40. The absorbent pants according to claim 38, wherein the core pack is arranged with the liquid barrier sheet facing toward the inner elastic material sheet of the oar pants.

41. The absorbent pants according to claim 37, wherein the sheet of elastic medal is liquid-impermeable, and wherein the core pack is arranged with the liquid barrier sheet facing toward the liquid-impermeable sheet of elastic material.

42. The absorbent pants according to claim 38, wherein elastic members are secured between the inner elastic material sheet and the outer elastic material sheet to form waist elastic and/or leg elastic.

43. The absorbent pants according to claim 38, wherein elastic members are secured between the inner elastic material sheet and the outer elastic material sheet with the elastic members being extended no more than about 10% and with the inner elastic material sheet and the outer elastic material sheet being substantially unstretched.

44. The absorbent article as set forth in claim 38, wherein the outer elastic material sheet comprises a nonwoven elastic material or an elastic textile.

45. The absorbent pants according to claim 37, further comprising elastic members secured to the sheet of elastic material forming the outer pants with the elastic members being extended no more than about 10%.

46. The absorbent pants according to claim 29, wherein elastic members are arranged around the waist opening and form waist elastic and/or are arranged around the leg openings and form leg elastic.

47. The absorbent pants according to claim 46, wherein the elastic members are secured to the absorbent pants with the elastic members being extended by at most about 10%.

48. The absorbent pants according to claim 47, wherein the extensibility of the sheet of elastic material is at least 80% in the transverse direction of the diaper pants.

49. The absorbent pants according to claim 47, wherein the extended circumference of the waist opening is at least 80% greater than the unextended circumference.

50. The absorbent pants according to claim 49, wherein the extensibility of the sheet of elastic material is at least 80% in the transverse direction of the absorbent pants.

51. The absorbent pants according to claim 29, wherein the absorbent pants can support a weight of 200 grams.

52. The absorbent pants according to claim 29, wherein the absorbent pants can support a weight of 1000 grams.

53. The absorbent pants according to claim 29, wherein the sheet of elastic material is substantially unstretched and the absorbent pants have a planar shape when the pants are not being worn, and wherein the sheet of elastic material stretches in at least the transverse direction to fit a wearer's body when the pants are worn.

54. The absorbent pants according to claim 29, further comprising:
a liquid-permeable inner sheet arranged at a side of the absorbent core intended to face toward a wearer's body.

55. The absorbent pants according to claim 54, wherein the liquid-permeable inner sheet is non-elastic.

56. The absorbent pants according to claim 54, wherein the liquid-permeable inner sheet is elastic.

57. The absorbent pants according to claim 56, wherein the elastic liquid-permeable inner sheet forms an inner surface of the absorbent pants.

58. Absorbent pants with a longitudinal direction and a transverse direction at right angles to the longitudinal direction, comprising:
a front portion, a rear portion and an intermediate crotch portion; a front edge and a rear edge extending substantially in the transverse direction and forming a waist opening having an unextended circumference and an extended circumference;
two side edges extending substantially in the longitudinal direction and forming two leg openings;
a sheet of elastic material arranged at least along the waist opening and extending at least from the waist opening to the leg openings;
a core pack including
a liquid barrier sheet, a liquid-permeable sheet, and absorption core having absorbent material and being arranged between the liquid barrier sheet and the liquid-permeable sheet,
the sheet of elastic material being secured directly to the core pack in a substantially unstretched state;
elastic members secured to the sheet of elastic material with the sheet of elastic material in a substantially unstretched state and the elastic members being extended at most about 10%.

59. Absorbent pants with a longitudinal direction and a transverse direction at right angles to the longitudinal direction, comprising:
a front portion, a rear portion and an intermediate crotch portion; a front edge and a rear edge extending substantially in the transverse direction and forming a waist opening having an unextended circumference and an extended circumference;
two side edges extending substantially in the longitudinal direction and forming two leg openings;
a sheet of elastic material arranged at least along the waist opening and extending at least from the waist opening to the leg openings;
a core pack including
a liquid barrier sheet, a liquid-permeable sheet, and absorption core having absorbent material and being arranged between the liquid barrier sheet and the liquid-permeable sheet,
the sheet of elastic material being secured directly to the core pack in a substantially unstretched state and being arranged on a side of the core pack intended to face away from a wearer's body during use;
a liquid-permeable inner sheet arranged at a side of the core pack intended to face the wearer in use; and
elastic members secured to the sheet of elastic material with the sheet of elastic material in a substantially unstretched state and the elastic members being extended at most about 10%.

60. The absorbent pants according to claim 1, wherein the sheet of elastic material is secured to the absorption core in a substantially unstretched state such that the absorbent pants has a smooth surface in a region of the elastic material when the absorbent pants are in an unstretched state.

61. The absorbent pants according to claim 29, wherein the sheet of elastic material is secured to the absorption core in a substantially unstretched state such that the absorbent pants has a smooth surface in a region of the elastic material when the absorbent pants are in an unstretched state.

62. The absorbent pants according to claim 58, wherein the sheet of elastic material is secured to the absorption core in a substantially unstretched state such that the absorbent pants has a smooth surface in a region of the elastic material when the absorbent pants are in an unstretched state.

63. The absorbent pants according to claim 59, wherein the sheet of elastic material is secured to the absorption core in a substantially unstretched state such that the absorbent pants has a smooth surface in a region of the elastic material when the absorbent pants are in an unstretched state.

* * * * *